(12) United States Patent
Kramer et al.

(10) Patent No.: US 6,352,532 B1
(45) Date of Patent: Mar. 5, 2002

(54) ACTIVE LOAD CONTROL OF ULTRASONIC SURGICAL INSTRUMENTS

(75) Inventors: Kenneth S. Kramer, Loveland; Kevin L. Houser, Springboro, both of OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/460,698

(22) Filed: Dec. 14, 1999

(51) Int. Cl.⁷ .............................................. A61B 18/04
(52) U.S. Cl. ............................. 606/41; 606/38; 601/2; 600/439
(58) Field of Search ............................. 606/32, 34, 37, 606/38, 41, 42, 205, 206; 601/2; 600/437, 439, 442

(56) References Cited

U.S. PATENT DOCUMENTS

| | | |
|---|---|---|
| 4,714,865 A | 12/1987 | Chin et al. |
| 5,151,085 A | 9/1992 | Sakurai et al. |
| 5,184,605 A | 2/1993 | Grzeszykowski |
| 5,197,371 A | 3/1993 | Van der Heijden et al. |
| 5,275,166 A | 1/1994 | Vaitekunas et al. |
| 5,293,809 A | 3/1994 | Van der Heijden et al. |
| 5,357,423 A | 10/1994 | Weaver et al. |
| 5,449,370 A | 9/1995 | Vaitekunas |
| 5,460,595 A | 10/1995 | Hall et al. |
| 5,540,684 A | 7/1996 | Hassler, Jr. |
| 5,543,695 A | 8/1996 | Culp et al. |
| 5,558,671 A | 9/1996 | Yates |
| 5,599,350 A | 2/1997 | Schulze et al. |
| 5,630,420 A | 5/1997 | Shi et al. |
| 5,637,947 A | 6/1997 | Kising et al. |
| 5,645,210 A | 7/1997 | Toner et al. |
| 5,707,369 A | 1/1998 | Vaitekunas et al. |
| 5,776,130 A | 7/1998 | Buysse et al. |
| 5,808,665 A | 9/1998 | Green |
| 5,859,934 A | 1/1999 | Green |
| 5,928,846 A | 7/1999 | Yamashita et al. |
| 5,931,832 A | 8/1999 | Jensen |
| 5,935,143 A | 8/1999 | Hood |
| 5,947,984 A | 9/1999 | Whipple |
| 5,950,629 A | 9/1999 | Taylor et al. |
| 5,954,692 A | 9/1999 | Smith et al. |
| 5,976,122 A | 11/1999 | Madhani et al. |

Primary Examiner—David O. Reip
Assistant Examiner—Julian W. Woo
(74) Attorney, Agent, or Firm—Verne E. Kreger, Jr.

(57) ABSTRACT

Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. The present invention provides a surgical instrument including force feedback system, in a closed loop arrangement that modulates the force applied to tissue from a surgical instrument. A generator provides electrical energy to the surgical instrument and an electrical signal representative of the generator load. The surgical instrument includes a handle that includes an actuating lever, and an end-effector located at the distal end of the handle. A force responsive element is operatively coupled to the actuating lever and the end-effector, wherein the force responsive element is adapted to alter a force on the end-effector in response to the electrical signal from the generator.

10 Claims, 7 Drawing Sheets

ACTIVE LOAD CONTROL OF ULTRASONIC SURGICAL INSTRUMENTS

FIELD OF THE INVENTION

The present invention relates, in general, to ultrasonic surgical instruments and, more particularly, to active load feedback control of ultrasonic surgical clamping instruments.

BACKGROUND OF THE INVENTION

Ultrasonic instruments, including both hollow core and solid core instruments, are used for the safe and effective treatment of many medical conditions. Ultrasonic instruments, and particularly solid core ultrasonic instruments, are advantageous because they may be used to cut and/or coagulate organic tissue using energy in the form of mechanical vibrations transmitted to a surgical end-effector at ultrasonic frequencies. Ultrasonic vibrations, when transmitted to organic tissue at suitable energy levels and using a suitable end-effector, may be used to cut, dissect, or cauterize tissue. Ultrasonic instruments utilizing solid core technology are particularly advantageous because of the amount of ultrasonic energy that may be transmitted from the ultrasonic transducer through the waveguide to the surgical end-effector. Such instruments are particularly suited for use in minimally invasive procedures, such as endoscopic or laparoscopic procedures, wherein the end-effector is passed through a trocar to reach the surgical site.

Ultrasonic vibration is induced in the surgical end-effector by, for example, electrically exciting a transducer which may be constructed of one or more piezoelectric or magnetostrictive elements in the instrument handpiece. Vibrations generated by the transducer section are transmitted to the surgical end-effector via an ultrasonic waveguide extending from the transducer section to the surgical end-effector.

U.S. Pat. No. 5,322,055 describes an ultrasonic surgical apparatus that includes a surgical instrument having a transducer for converting an electrical signal into longitudinal vibratory motion. The longitudinal vibratory motion is transmitted to an ultrasonic blade that is connected to the handpiece. An accessory is releasably connected to the handpiece to enable clamping of tissue against the vibrating blade to afford improved coagulating and cutting of tissue. In U.S. Pat. No. 5,322,055 scissors-like grips actuate a pivoted clamp jaw along one side of the ultrasonically vibrating blade to compress and bias tissue against the blade in a direction which is substantially normal to the direction of longitudinal vibratory motion. U.S. Pat. No. 5,322,055 is hereby incorporated herein by reference.

Hemostatic devices have been described in various instruments for cutting, cauterization, coagulation or tissue welding. Most of the devices used are either monopolar or bipolar, for example, bipolar forceps, monopolar or bipolar scissors, and cutting and coagulating devices. See, for example, U.S. Pat. No. 5,707,369 that describes a temperature feedback system for closed loop control of the tissue temperature induced by the surgical instrument wherein a function of the temperature is used to determine when coagulation of tissue has occurred to a desired degree.

Although open loop electrosurgical and ultrasonic instruments have been used successfully to control bleeding during surgical procedures, when such instruments are used, the primary control is the experience of the surgeon who responds to what is observed to be happening to the tissue as it is treated with energy. Often, particularly for endoscopic procedures, surgeons cannot readily see what is happening to the tissue. Also, the change in tissue properties due to the energy may occur so quickly so as not to afford time for the surgeon to react soon enough to turn off the energy to the instrument. As a result, the tissue treatment may not be as precisely controlled as may be desirable. Some problems that may occur include tissue charring, sticking of the tissue to the electrodes of electrosurgical instruments, and over or under treatment of the tissue.

There is a continuing need to improve the control of energy delivery to tissue and/or to determine when tissue treatment has reached an optimal or desired level. The amount of ultrasonic energy coupled into tissue is a function of the force applied to the tissue by the ultrasonic end-effector. Prior instruments, such as those described in U.S. Pat. No. 5,947,984 hereby incorporated herein by reference, have limited the maximum amount of force that a surgeon could apply to tissue. However this is a single maximum set-point, and does not actively control the force applied to the tissue below the set limit. In particular there is a need to provide a device and method for active control of ultrasonic instruments that must perform both cutting and coagulating functions.

SUMMARY OF THE INVENTION

The present invention meets the needs described above by providing a system including a force feedback system for use in surgical procedures. The force feedback system is a closed loop arrangement that can modulate the force applied to tissue from a surgical instrument. A generator produces an electrical signal, which has a load parameter indicative of generator load. A load parameter may be, for example, current, voltage, impedance or temperature. A surgical instrument is electrically connected to the generator. The surgical instrument includes a handle that includes an actuating lever, and an end-effector located at the distal end of the handle. A force responsive element is operatively coupled to the actuating lever and the end-effector, wherein the force responsive element is adapted to alter a force on the end-effector in response to the electrical signal from the generator.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

The present invention relates, in general, to ultrasonic surgical clamping instruments and, more particularly, to active load feedback control of ultrasonic surgical clamping instruments. The present invention will be described in combination with ultrasonic instruments described herein such as, for example, an ultrasonic clamp coagulator instrument described in U.S. Pat. No. 5,947,984. Such description is exemplary only, and is not intended to limit the scope and applications of the invention.

Figure 1:
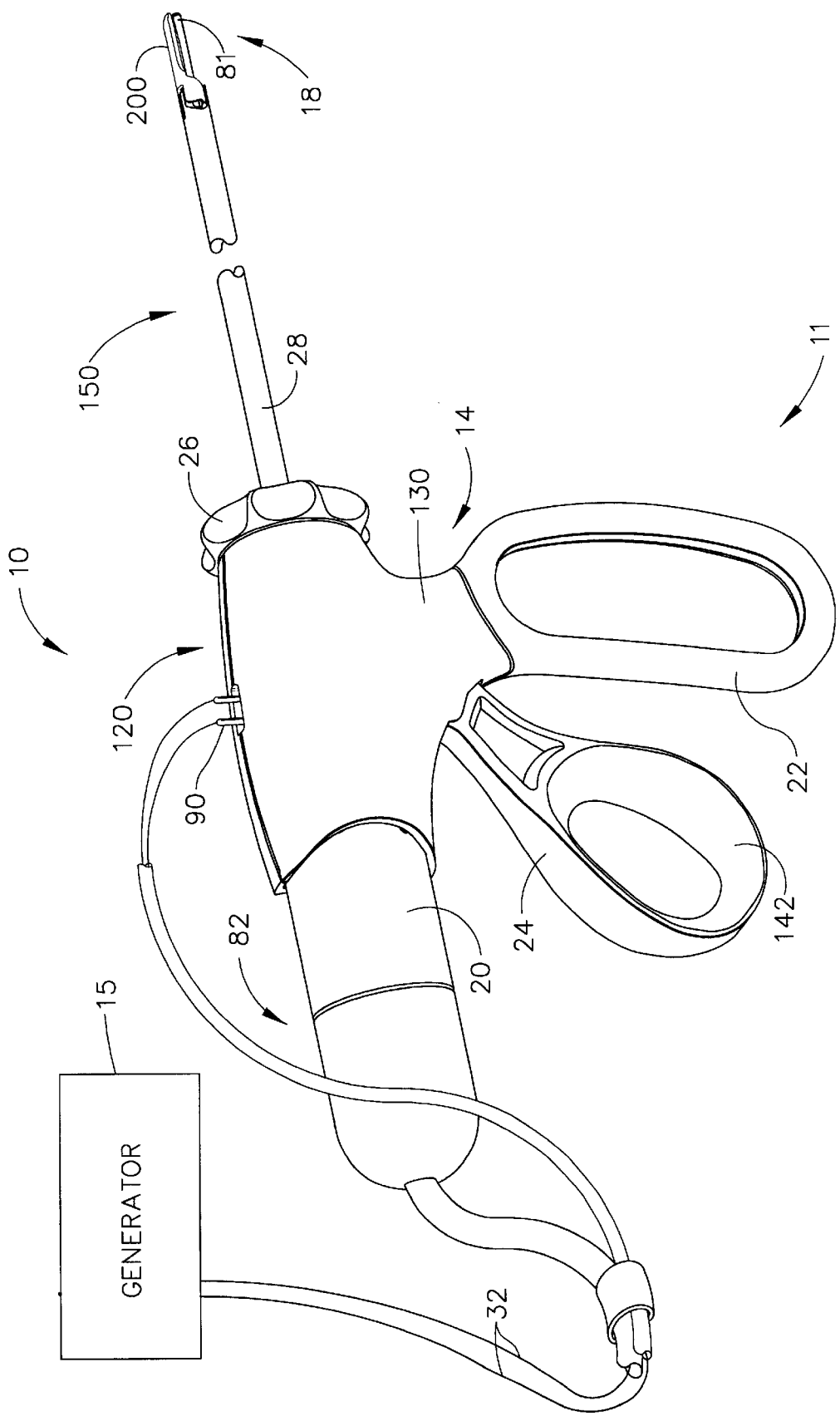
FIG. 1 is a perspective view illustrating a surgical system including an actively controlled ultrasonic surgical shears according to the present invention, wherein the surgical shears are illustrated in combination with an ultrasonic transducer and a plan view of an ultrasonic signal generator.

FIG. 1 illustrates ultrasonic system 10 comprising an ultrasonic signal generator 15 with an ultrasonic surgical instrument 11. Ultrasonic surgical instrument 11 includes a sandwich type ultrasonic transducer 82, a hand piece housing 20, and a clamp coagulator 120 in accordance with the present invention. Clamp coagulator 120 may be used for open or laparoscopic surgery. Clamp coagulator 120 includes instrument handle 14, and elongated member 150 including ultrasonic end-effector 18. End-effector 18 includes a clamp arm assembly 200 and a blade 81. Ultrasonic transducer 82 includes a power supply cable 32. Ultrasonic transducer 82, which may also be referred to as a handpiece, comprises transduction elements (not shown), preferably piezoceramic elements, for converting an electrical signal, for example, a 55,000 Hz sinusoidal waveform, into a mechanical longitudinal vibration. A suitable ultrasonic handpiece is available from Ethicon Endo-Surgery, Inc. as make ULTRACISION HARMONIC SCALPEL® and model HP051.

Power supply cable 32 transmits electrical energy from the ultrasonic signal generator 15 to ultrasonic transducer 82. Ultrasonic transducer 82 converts electrical energy into ultrasonic energy in the form of mechanical motion. A suitable generator is available as model number GEN01, from Ethicon Endo-Surgery Inc., Cincinnati, Ohio. The ultrasonic energy is transmitted from ultrasonic transducer 82, through the clamp coagulator 120, to the end-effector 18.

A surgical instrument such as, for example, clamp coagulator 120, places a load on the output stage of generator 15. A surgical instrument load is the load seen by the output stage of generator 15, that is controlling and driving the surgical instrument. A portion of the surgical instrument load may include tissue load, as end-effector 18 is used to affect tissue.

Figure 2:
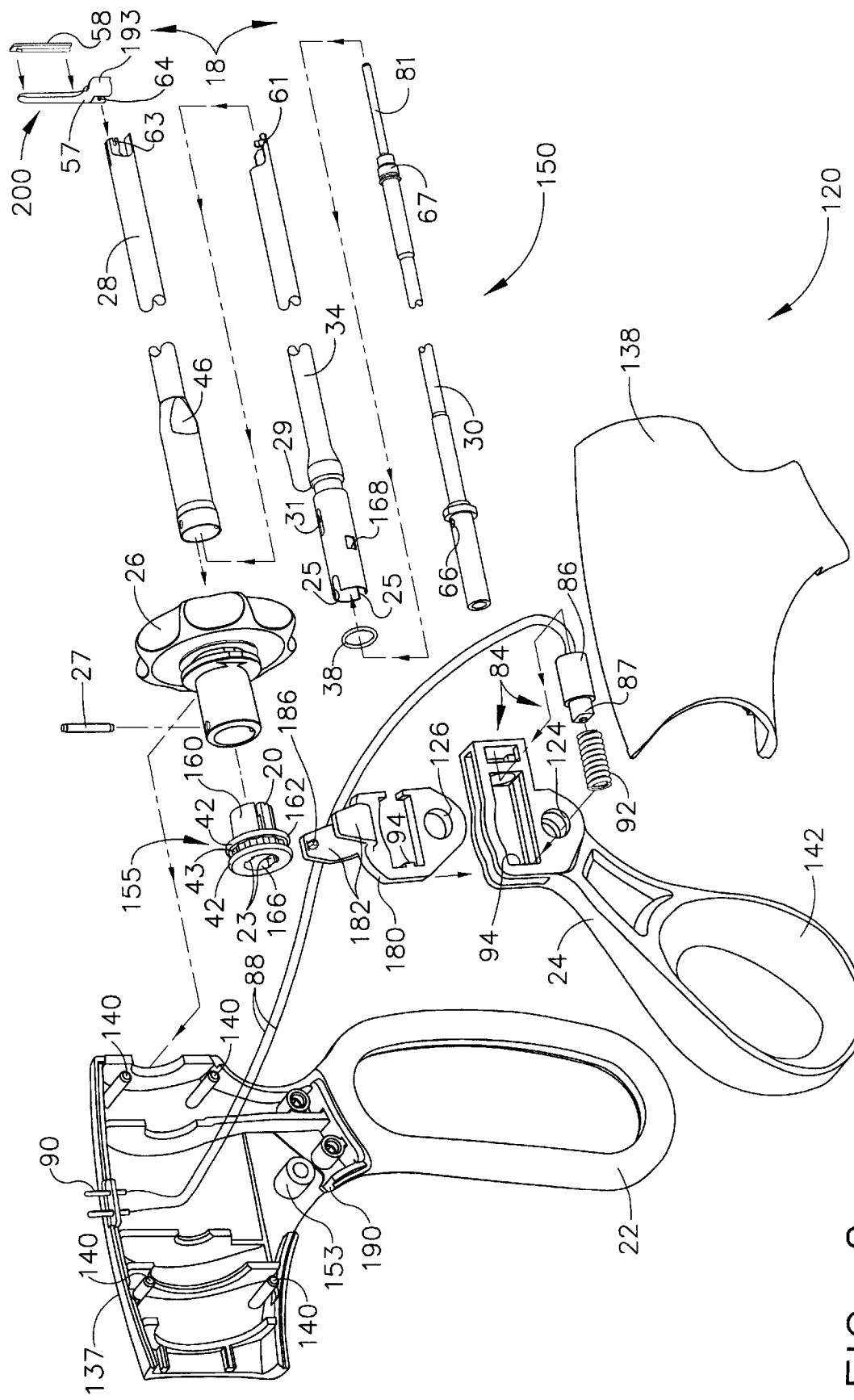
FIG. 2 is an exploded perspective view of a first embodiment of a surgical instrument according to the present invention.
Figure 3:
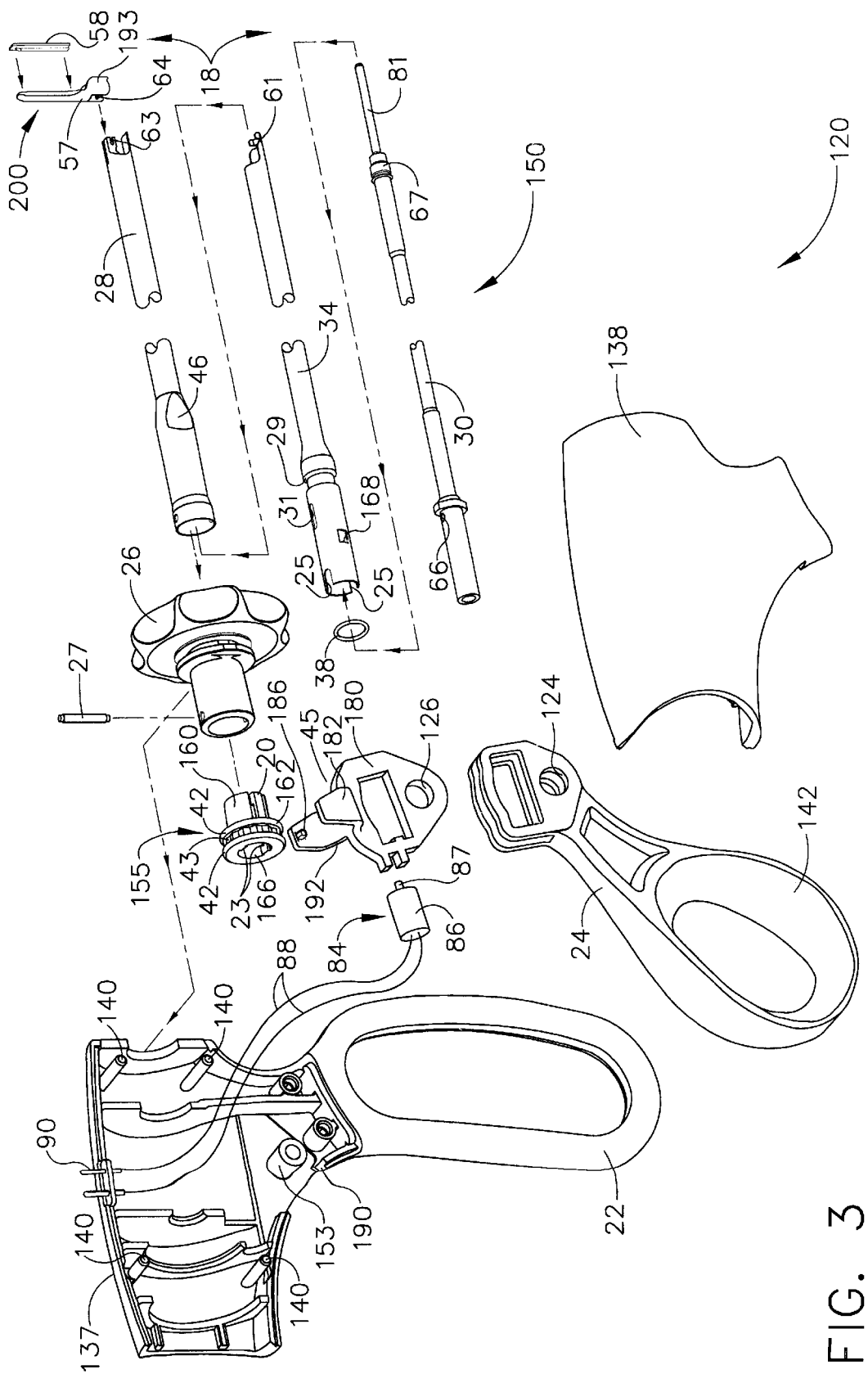
FIG. 3 is an exploded perspective view of a second embodiment of a surgical instrument according to the present invention.

Referring now to FIGS. 2, and 3, clamp coagulator 120 is preferably attached to and removed from the ultrasonic transducer 82 as a unit. The proximal end of the clamp coagulator 120 preferably acoustically couples to ultrasonic transducer 82 as shown in FIG. 1. It will be recognized that the clamp coagulator 120 may be coupled to the ultrasonic transducer 82 by any suitable means.

Referring to FIGS. 1 through 3, the elongated member 150 can be selectively rotated with respect to the instrument housing 130 as further described below. The instrument housing 130 (FIG. 1) includes a actuation trigger 24, and a finger grip 22, a left shroud 137 and a right shroud 138 (FIGS. 2 and 3). Elongated member 150 includes a support tube designated as outer sheath 28, ultrasonic waveguide 30, rotation knob 26, actuating arm 34, O-ring 38, pin 27, tubular collar 160, and end-effector 18. End-effector 18 includes ultrasonic blade 81 and clamp arm assembly 200, which comprises clamp arm 57 and tissue pad 58. Actuating arm 34 includes keyways 25, openings 168, pin-slot 31, O-ring groove 29, and lever-arms 61.

The right shroud 138 is adapted to snap fit on the left shroud 137. The right shroud 138 is preferably coupled to the left shroud 137 by a plurality of inwardly facing prongs 70 (not shown) formed on the right shroud 138. The plurality of prongs 70 are arranged for engagement in corresponding holes or apertures 140, which are formed in the left shroud 137. When the left shroud 137 is attached to the right shroud 138, a cavity is formed therebetween to accommodate various components, such as an active force mechanism as further described below.

Indexing mechanism 155 is disposed in the cavity of the instrument housing 130. The indexing mechanism 155 is preferably coupled or attached on actuating arm 34 to translate movement of the actuation trigger 24 to linear motion of the actuating arm 34 to open and close the clamp arm assembly 200. When the actuation trigger 24 is moved toward the finger grip 22, the indexing mechanism 155 slides the actuating arm 34 rearwardly to pivot the clamp arm assembly 200 into a closed position. The movement of the actuation trigger 24 in the opposite direction slides the indexing mechanism 155 to displace the actuating arm 34 in the opposite direction, i.e., forwardly, and hence pivot the clamp arm assembly 200 into its open position. Actuation trigger 24 includes a thumb loop 142 with a first hole 124. A yoke 180 includes a second hole 126. A pivot pin 153 is disposed through first hole 124 and second hole 126 to allow pivoting.

The indexing mechanism 155 also provides a ratcheting mechanism to allow the elongated member 150 to rotate about its longitudinal axis relative to instrument housing 130. The rotation of the elongated member 150 enables the clamp arm assembly 200 to be turned to a selected or desired angular position. The indexing mechanism 155 preferably includes a tubular collar 160 and yoke 180. The tubular collar 160 of the indexing mechanism 155 is preferably snapped onto the proximal end of the actuating arm 34 and keyed into opposing openings 168. The tubular collar 160 is preferably fabricated from polyetherimide. It is contemplated that the tubular collar 160 may be constructed from any suitable material. Tubular collar 160 may also be keyed to actuating arm 34 by keys 23 insertable into keyways 25.

The tubular collar 160 preferably includes an enlarged section 162, and a bore 166 extending therethrough. The enlarged section 162 preferably includes rings 42 formed around the periphery of the tubular collar 160 to form groove 43. The groove 43 has a plurality of detents or teeth 44 (see FIGS. 4 and 5) for retaining the elongated member 150 in different rotational positions as the elongated member 150 is rotated about its longitudinal axis. Preferably, the groove 43 has twelve ratchet teeth to allow the elongated portion to be rotated in twelve equal angular increments of approximately 30 degrees. It is contemplated that the tubular collar 160 may have any number of teeth-like members. It will be recognized that the teeth-like members may be disposed on any suitable part of the tubular collar 160 without departing from the scope and spirit of the present invention.

Yoke 180 generally includes a holding or supporting member 182. The supporting member 182 is preferably semi-circular and has a pair of opposing pawls 186 that extend inwardly to engage with the teeth 44 of the tubular collar 160. It is contemplated that the pawls 186 may be disposed on any suitable part of the yoke 180 for engagement with the teeth 44 of the tubular collar 160. It will also be recognized that the yoke 180 may have any number of ratchet arms.

The clamp arm assembly 200 is pivotally connected to the distal end of outer sheath 28. Tissue pad 58, preferably formed from Teflon or other suitable low-friction material, is mounted on the surface of the clamp arm for cooperation with the blade 81, with pivotal movement of the clamp arm assembly 200 positioning the tissue pad 58 in substantially parallel relationship to, and in contact with, the blade 81. By this construction, tissue to be clamped is grasped between the tissue pad 58 and the blade 81. Tissue pad 58 is preferably provided with a sawtooth-like configuration to enhance the gripping of tissue in cooperation with the blade 81.

Pivotal movement of the clamp arm assembly 200 with respect to the end-effector is effected by the provision of at least one, and preferably a pair of levers 193 of the clamp arm assembly 200 at the proximal end thereof. The levers 193 are positioned on respective opposite sides of the blade 81, and are in operative engagement with lever arms 61 of the reciprocable actuating arm 34. Reciprocal movement of the actuating arm 34, relative to the outer tubular sheath 160 and the blade 81, thereby affects pivotal movement of the clamp arm assembly 200 relative to the blade 81. The levers 193 can be respectively positioned in a pair of openings defined by the lever arms 61, or otherwise suitably mechanically coupled herewith, whereby reciprocal movement of the actuating member acts through the lever arms 61 and levers 193 to pivot the clamp arm.

Pawls 186 transfer opening force to actuating arm 34 through tubular collar 160, resulting in the opening of clamp arm assembly 200. The yoke 180 is preferably fabricated from polycarbonate. The yoke 180 may also be made from a variety of materials including other plastics, such as ABS, NYLON, or polyetherimide. It is contemplated that the yoke 180 may be constructed from any suitable material.

Yoke 180 also transfers a closing force to clamp arm assembly 200 as actuation trigger 24 is moved toward instrument housing 130. Actuator travel stop 190 contacts actuation trigger 24 at the bottom of the stroke of actuation trigger 24, stopping any further movement, or over-travel, of actuation trigger 24.

To assemble the instrument 11 and accessory clamp coagulator 120, the clamp coagulator 120 is screw-threaded onto the end of ultrasonic transducer 82. In using the device it will be appreciated that the clamp can be used to coagulate and cut with ultrasonic energy applied, can be used to grasp tissue without application of ultrasonic energy, can be used to coagulate/cut with the clamp arm assembly 200 open and tissue unclamped, can be used to probe or manipulate tissue without application of ultrasonic energy, and can be used, with the clamp arm assembly 200 closed, for blunt dissection. The desired clamp arm assembly 200 rotational alignment is accomplished by use of rotation knob 26, that can be rotated while holding the instrument housing 130 to thereby rotate the elongated member 150 relative to the instrument housing 130. The detents provided by teeth 44 maintain this selected rotary alignment. The scissors-like grips are activated to close the clamp arm assembly 200 and ultrasonic power may be applied by activating a switch such as, for example, a foot switch. The longitudinal blade 81 vibration relative to the clamp arm assembly 200 couples to the tissue, causing coagulation, cutting or other desirable effects. Desirable tissue effects can be optimized by active pressure control as described below.

Figure 4:
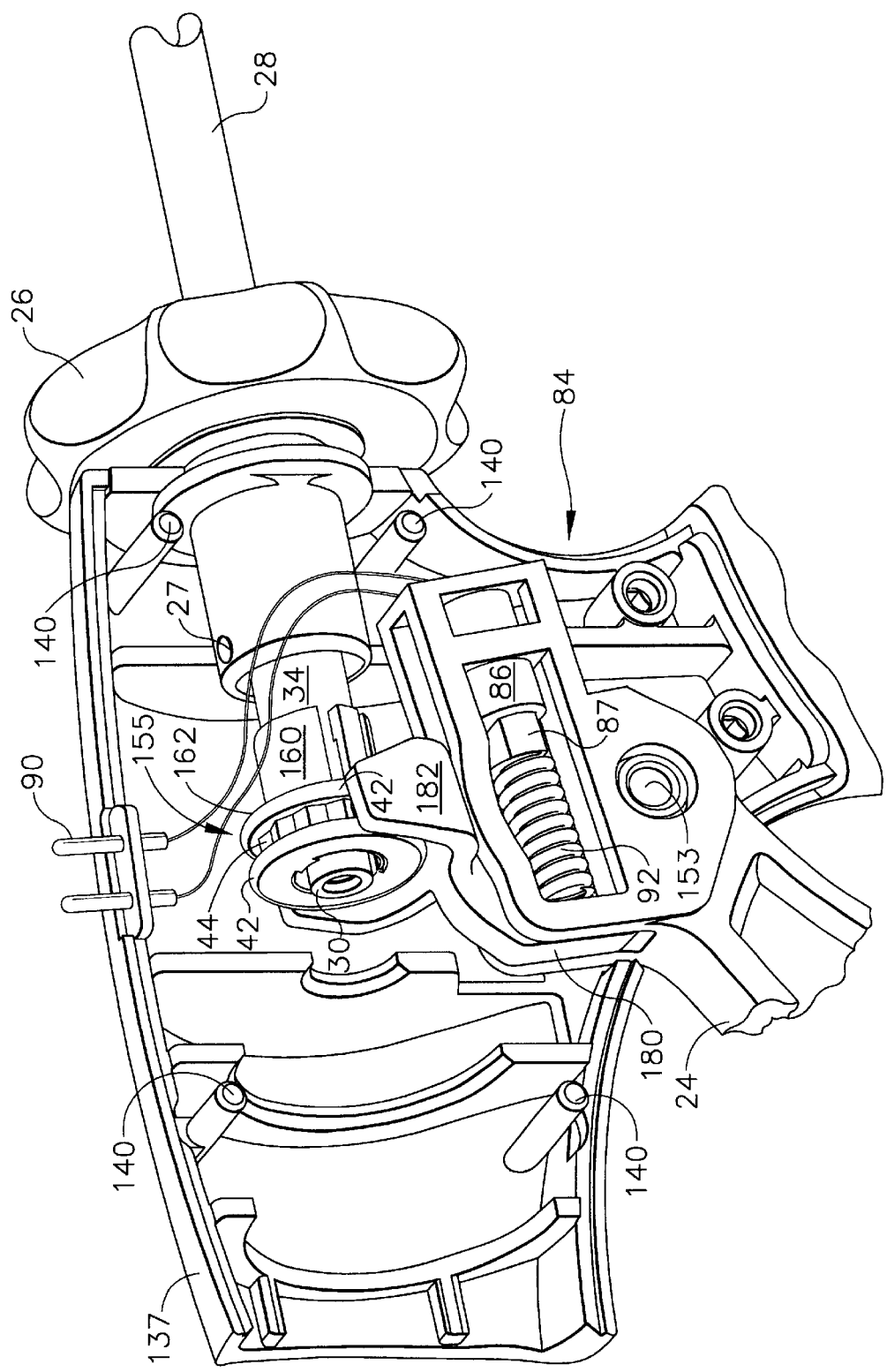
FIG. 4 is a partial cutaway perspective view of the internal mechanism of the surgical instrument shown in FIG. 2.
Figure 5:
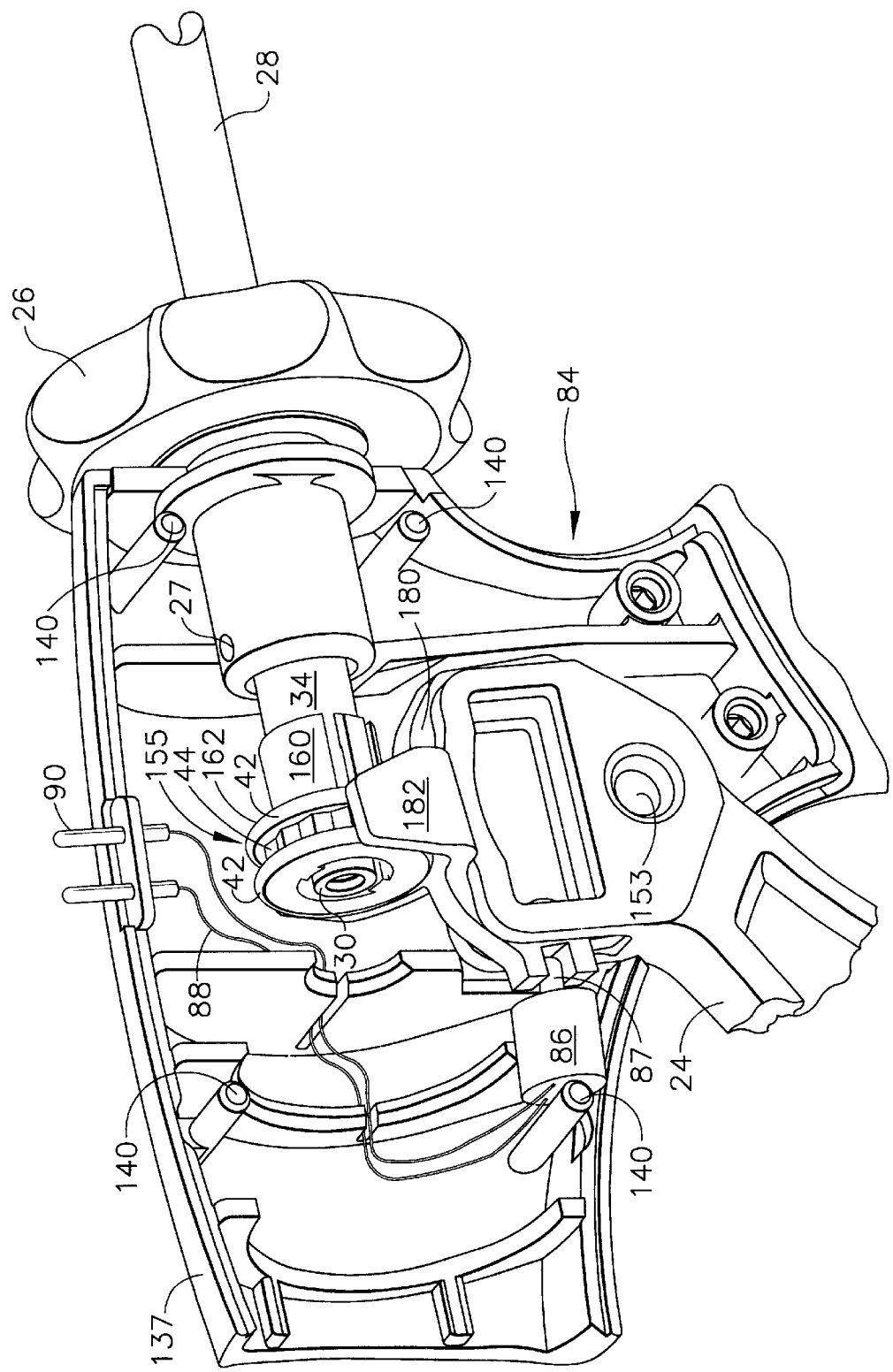
FIG. 5 is a partial cutaway perspective view of the internal mechanism of the surgical instrument shown in FIG. 3.
Figure 6:
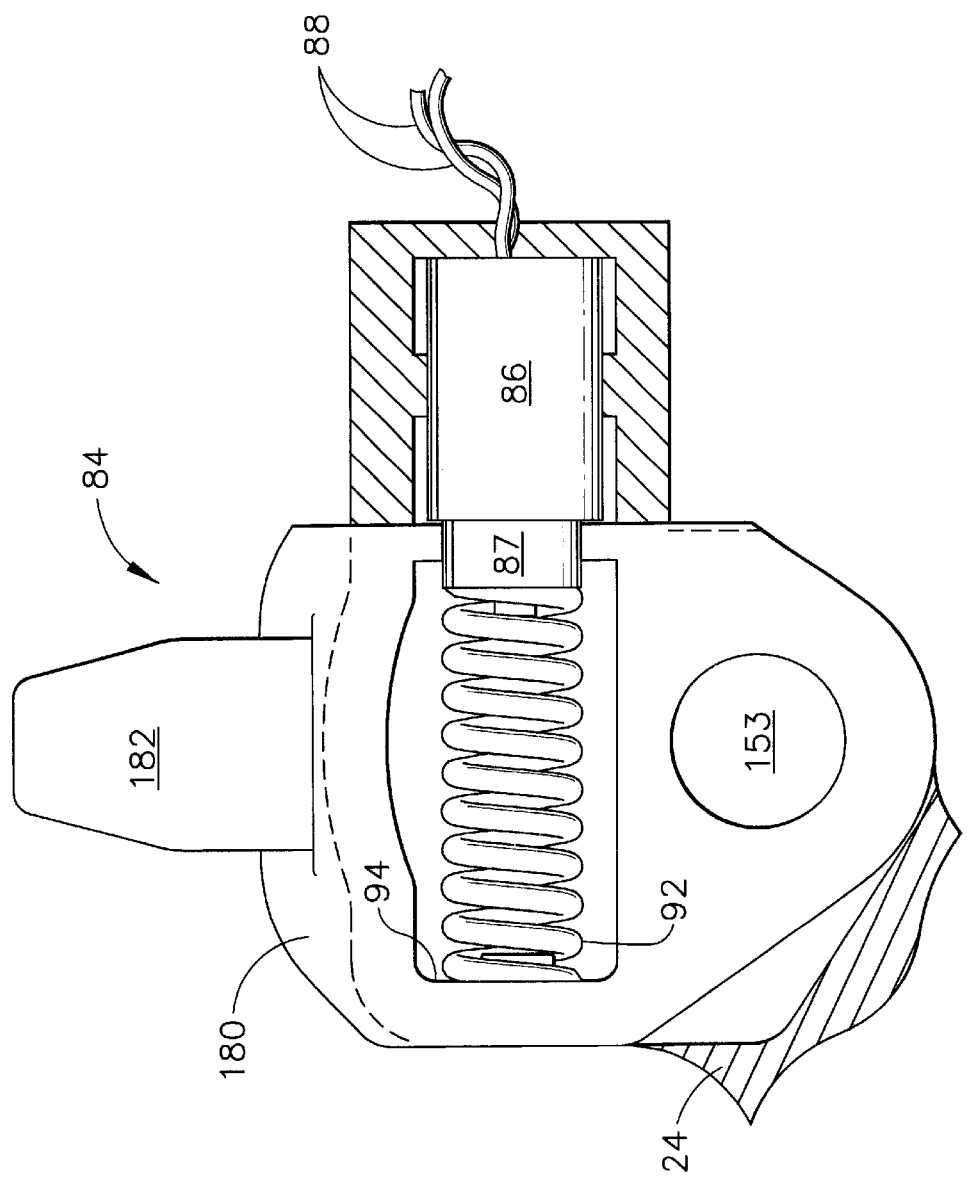
FIG. 6 is a side view of the force mechanism of the surgical instrument shown in FIGS. 2 and 4.
Figure 7:
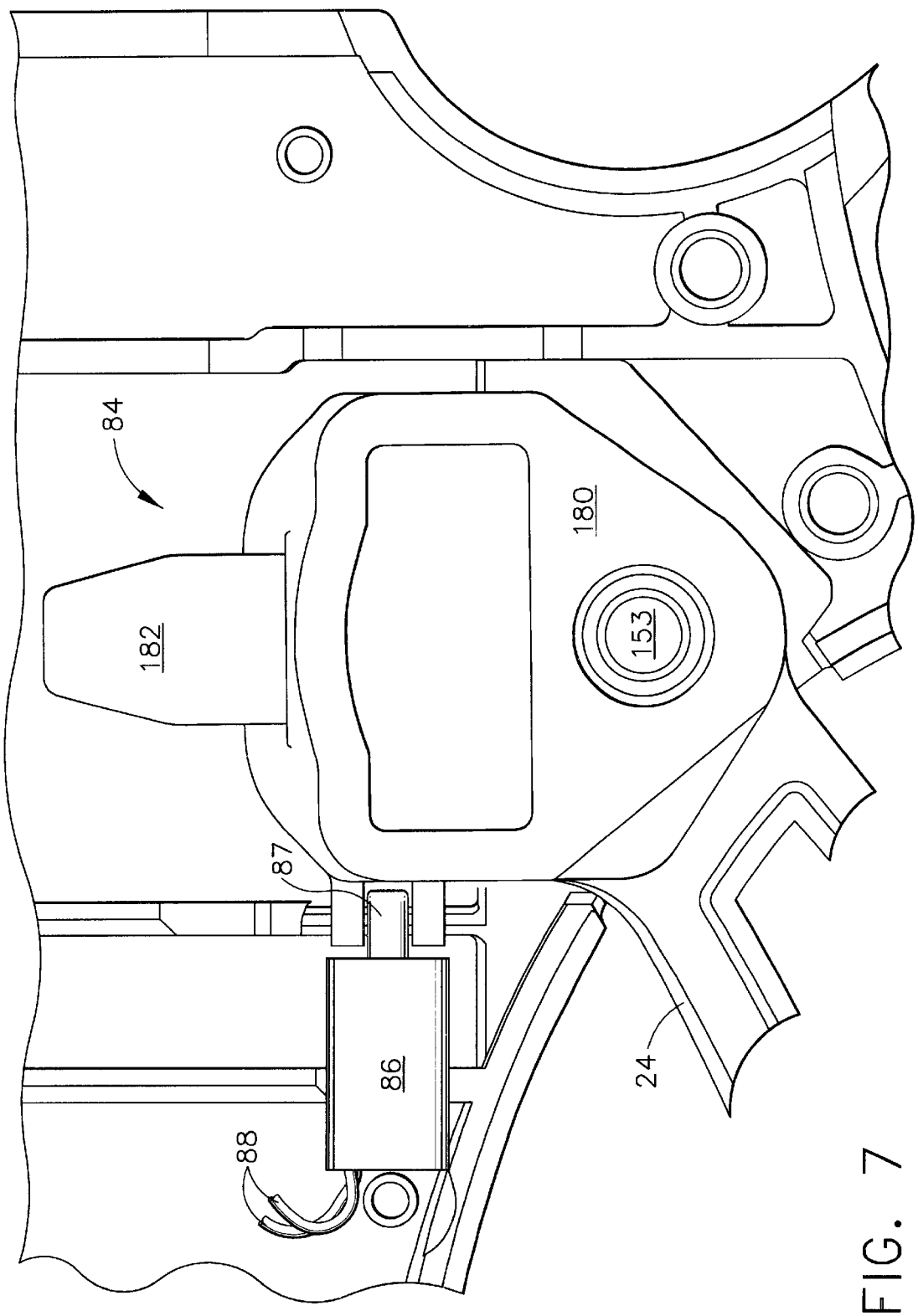
FIG. 7 is a side view of the force mechanism of the surgical instrument shown in FIGS. 3 and 5.

Active load control of clamp arm 57 against blade 81 is performed by a pressure control system 84 illustrated in FIGS. 2 through 7. A first embodiment of a pressure control system 84 is illustrated in FIGS. 2, 4, and 6. A second embodiment of a pressure control system 84 is illustrated in FIGS. 3, 5, and 7. Both embodiments are illustrated utilizing a pressure transducer 86 including a piston 87, such as, for example, an electro-mechanical solenoid. It will be understood by those skilled in the art that any force or pressure transducer may be utilized with pressure control system 84, such as, for example, servo-motors, hydraulics, pneumatics, and bi-metallics.

Referring to the first embodiment illustrated in FIGS. 2, 4 and 6, pressure control system 84 includes pressure transducer 86, wires 88, connector 90, spring 92, spring cage 94, yoke 180, and actuating arm 34. Pressure transducer 86 is electrically connected to ultrasonic signal generator 15 via wires 88, through connector 90 and cable 32 (FIG. 1). Pressure transducer 86 changes in response to an electrical signal from ultrasonic signal generator 15, altering the force or load exerted from actuating arm 34, through pressure control system 84, to end-effector 18.

As illustrated in FIGS. 4 and 6, pressure transducer 86 actively alters spring 92 compression. Actuation trigger 24 delivers force through spring 92 to yoke 180. As spring 92 is compressed, or released, the force delivered to end-effector 18 can be actively altered. Ultrasonic signal generator 15 may be programmable such that, for example, when an overload condition is detected by ultrasonic signal generator 15, an electrical signal may be sent to pressure transducer 86 causing pressure transducer 86 to release compression of spring 92, thereby mitigating the overload condition.

The load parameter for voltage in the ultrasonic signal generator 15 in, for example, the GEN01 generator disclosed previously, may be found on the generator PC board at location TP6. TP6 is illustrated in Appendix B of the Generator PCB schematic, which may be found in the ULTRACISION HARMONIC SCALPEL service manual. The GEN01 generator attempts to maintain constant current to the transducer 82. Therefore, voltage is adjusted as load varies, such that the voltage at TP6 is proportional to tissue load. Ultrasonic signal generator 15 may be programmed such that when TP6 reaches a set-point such as, for example, 200 Volts DC, the electrical signal is sent to pressure transducer 86 causing pressure transducer 86 to release compression of spring 92. When compression of spring 92 is released, the force that is transferred through the yoke 180 to actuating arm 34 reduces the force of clamp arm assembly 200 against blade 81. As may be understood by those skilled in the art, ultrasonic signal generator 15 may be programmed for other conditions such as, for example, a constant current load parameter, a constant voltage load parameter, an impedance parameter, an increased load after a set-point, a decreased load after a set-point, or a constantly decreasing load. Further, the temperature at the end effector is an indicator of load on the generator. A temperature feedback system, such as described in U.S. Provisional application Ser. No. 60/136,106, which is incorporated by reference herein, can be implemented to generate a electrical signal indicative of tissue load from generator 15 to pressure transducer 86.

In the first embodiment of the present invention, the active load control of pressure control system 84 worked in conjunction with the ultrasonic system 10 operator through actuation trigger 24. The operator can over-ride the active system by manually modulating the actuation trigger 24. Referring now to FIGS. 3, 5 and 7, a second embodiment of the present invention is illustrated wherein the operators' use of actuation trigger 24 can be over-ridden by pressure control system 84.

In the second embodiment, pressure transducer 86 delivers force directly to yoke 180. Pressure transducer 86 is rigidly attached to left shroud 137. Piston 87 is operatively connected to yoke 180. Yoke 180 may be rigidly attached to actuation trigger 24 by gluing, ultrasonic welding or the like. Alternately, yoke 180 may be flexibly mounted to actuation trigger 24 through a spring, such as described in U.S. Pat. No. 5,947,984. As piston 87 of pressure transducer 86 is extended or retracted, the force felt by the operator is reduced or enhanced respectively. Ultrasonic signal generator 15 may be programmable such that, for example, when an overload condition is detected by ultrasonic signal generator 15, an electrical signal may be sent to pressure transducer 86 causing piston 87 to retract, thereby decreasing the force of clamp arm assembly 200 against blade 81. As may be understood by those skilled in the art, ultrasonic signal generator 15 may be programmed for other conditions such as, for example, an increasing clamp arm force, a decreased clamp arm force, maintaining constant clamp arm force, an increased clamp arm force after a predetermined time, a decreased load after a set-point, or a constantly decreasing load.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A system for use in surgical procedures comprising:
   a generator, wherein said generator produces an electrical signal, said electrical signal having a load parameter indicative of a surgical instrument load on said generator;
   a surgical instrument electrically connected to said generator, said surgical instrument comprising:
      a handle comprising an actuating lever for operating an end-effector,
      wherein the end-effector is located at the distal end of said handle; and
      a force responsive element operatively coupled to said actuating lever and said end-effector, wherein said force responsive element is adapted to alter a force on said end-effector in response to said electrical signal from said generator.

2. A system for use in surgical procedures according to claim 1, wherein said load parameter is selected from the group consisting of voltage, current, impedance and temperature.

3. A system for use in surgical procedures according to claim 1, wherein said surgical instrument further comprises a transducer for converting electrical energy into mechanical motion at ultrasonic frequencies.

4. A system for use in surgical procedures according to claim 3, wherein said end-effector comprises a clamp arm and a blade responsive to the ultrasonic frequencies.

5. A system for use in surgical procedures according to claim 4, wherein said force responsive element is operatively coupled to said clamp arm to alter the force of said clamp arm against said blade during operation of said surgical instrument independently of said actuating lever.

6. An ultrasonic system for use in surgical procedures comprising:
   an ultrasonic signal generator, wherein said ultrasonic signal generator produces an electrical signal at an ultrasonic frequency, said electrical signal having a load parameter indicative of generator load;
   a transducer electrically connected to said generator, wherein said transducer is adapted to convert electrical energy from said ultrasonic signal generator into mechanical motion;
   an ultrasonic surgical instrument comprising:
      a handle assembly, wherein said handle assembly is operatively coupled to said transducer;
      a waveguide acoustically coupled to said transducer, wherein said waveguide is adapted to transmit ultrasonic energy therethrough;
      an end-effector located at the distal end of said waveguide;
      an actuation element, wherein said actuation element is operatively coupled to said end-effector; and
      a force responsive element electrically connected to said ultrasonic signal generator and operatively coupled to said actuation element, wherein said force responsive element is adapted to alter a force on said actuation element in response to said electrical signal from said ultrasonic signal generator.

7. A system for use in surgical procedures comprising:
   a generator, wherein said generator comprises a signal means for indicating generator load;
   a surgical instrument electrically connected to said generator, said surgical instrument comprising:
      an actuating means for actuating an end-effector means of said surgical instrument;
      wherein the end-effector means is engageable with tissue; and
      a force means operatively coupled to said actuating means and said end-effector means, for altering a force on said end-effector means in response to said signal means.

8. A system for use in surgical procedures according to claim 7, wherein said surgical instrument further comprises a transducer means for converting electrical energy into mechanical motion at ultrasonic frequencies.

9. A system for use in surgical procedures according to claims 8, wherein said end-effector means comprises a clamp means for clamping tissue and a blade means for delivering ultrasonic energy to tissue.

10. A method of modifying the force exerted by an electrosurgical instrument on tissue, said method comprising the steps of:
   a) clamping said tissue with an end-effector of the electrosurgical instrument;
   b) applying energy to said tissue through said surgical instrument;
   c) sensing the tissue load on the surgical instrument;
   d) providing an electrical feedback signal to the surgical instrument, the feedback signal having at least one component representative of the tissue load; and
   e) modifying the clamping force applied by the end-effector on the tissue in response to the electrical feedback signal.

* * * * *